United States Patent [19]
Levander et al.

[11] Patent Number: 6,085,745
[45] Date of Patent: Jul. 11, 2000

[54] PHARMACEUTICAL CONTAINER AND INHALER DEVICE

[75] Inventors: Gustav Levander; Fredrik Forssell; Jesper Sjögren, all of Helsingborg, Sweden

[73] Assignee: Pharmacia & UpJohn AB, Sweden

[21] Appl. No.: 08/907,702

[22] Filed: Aug. 8, 1997

[30] Foreign Application Priority Data

Jul. 25, 1997 [SE] Sweden ................................. 9702796

[51] Int. Cl.[7] .......................... A61M 15/00; A61M 16/00; B05D 7/14; B65D 83/06
[52] U.S. Cl. ...................... 128/203.15; 215/222; 215/225
[58] Field of Search ...................... 128/200.14, 200.23, 128/202.21, 202.27, 203.12, 203.15; 215/206, 208, 211, 214, 217, 219, 220, 221, 222, 225, 350, 331, 332; 222/498, 499, 519, 521, 522; 285/330, 921

[56] References Cited

U.S. PATENT DOCUMENTS

| | | | |
|---|---|---|---|
| 2,332,798 | 10/1943 | Hunn ................................. | 128/203.12 |
| 2,332,799 | 10/1943 | Hunn et al. ........................ | 128/203.12 |
| 3,072,276 | 1/1963 | Nichols .................................. | 215/222 |
| 3,450,290 | 6/1969 | Turner .................................... | 215/206 |
| 3,782,574 | 1/1974 | Rumble .................................... | 215/9 |
| 4,049,148 | 9/1977 | Suhr et al. ............................. | 215/214 |
| 4,095,718 | 6/1978 | Kong ....................................... | 215/223 |
| 4,119,232 | 10/1978 | Thornton ................................ | 215/222 |
| 4,156,489 | 5/1979 | Kong ....................................... | 215/214 |
| 4,157,142 | 6/1979 | Kong ....................................... | 215/223 |
| 4,228,012 | 10/1980 | Pall ........................................ | 210/238 |
| 4,434,903 | 3/1984 | Cooke . | |
| 4,444,327 | 4/1984 | Hedgewick ............................. | 215/211 |
| 4,739,754 | 4/1988 | Shaner ................................. | 128/203.15 |
| 4,846,168 | 7/1989 | Abiko et al. ........................ | 128/203.15 |
| 4,936,852 | 5/1990 | Zoltan et al. ....................... | 128/200.23 |
| 5,167,242 | 12/1992 | Turner et al. ........................ | 131/273 |
| 5,336,680 | 8/1994 | Nietupski ............................... | 514/354 |
| 5,400,808 | 3/1995 | Turner et al. ........................ | 131/270 |
| 5,413,386 | 5/1995 | Dal Palu ............................... | 285/158 |
| 5,421,482 | 6/1995 | Garby et al. ............................ | 222/36 |
| 5,462,181 | 10/1995 | Glynn .................................... | 215/204 |
| 5,466,020 | 11/1995 | Page et al. ............................. | 285/361 |
| 5,477,849 | 12/1995 | Fry ........................................ | 128/200.14 |
| 5,501,236 | 3/1996 | Hill et al. ............................... | 131/270 |
| 5,598,836 | 2/1997 | Larson et al. ..................... | 128/200.23 |
| 5,611,444 | 3/1997 | Garby et al. ......................... | 215/230 |
| 5,718,355 | 2/1998 | Garby et al. ............................ | 222/36 |
| 5,799,651 | 9/1998 | Garby et al. ........................ | 128/200.23 |

FOREIGN PATENT DOCUMENTS 158214  6/1984  Norway .

*Primary Examiner*—John G. Weiss
*Assistant Examiner*—Joseph F. Weiss, Jr.
*Attorney, Agent, or Firm*—Fulbright & Jaworski L.L.P.

[57] ABSTRACT

A pharmaceutical container and inhaler device having a mouthpiece and a cap which are rotatably connected to each other. For providing a certain child-resistance against disconnection, the mouthpiece has an external circumferential groove, whereas the cap is provided with an internal boss for engagement with the groove. There is an axial notch extending from the groove to the end of the mouthpiece and "traps" for the boss, in the form of recesses on the groove, are provided at either side of the notch.

7 Claims, 2 Drawing Sheets

PHARMACEUTICAL CONTAINER AND INHALER DEVICE

TECHNICAL FIELD

The present invention relates to a pharmaceutical container and inhaler device designed to prevent the easy pulling apart of two connected, mutually rotatable members, having circular cross sections, at least in the areas of connection.

CROSS-REFERENCE TO RELATED APPLICATIONS

Priority is claimed to Swedish patent application, SE 9702796-5, filed Jul. 25, 1997.

BACKGROUND OF THE INVENTION

It is of great importance that children do not easily get access to the interior of a container or bottle of pills or of an inhaler (which is of special relevancy in the present case), as the contents of such a container or inhaler can be dangerous for children. An inhaler can for example hold a nicotine containing ampoule, used to administer nicotine to a person, who is trying to abandon the habit of smoking cigarettes. The nicotine is very harmful for children.

When the two mutually rotatable members of the inventive inhaler have been connected or assembled (after an ampoule has been inserted therein), it will preferably be difficult or even virtually impossible for a child to disconnect or disassemble the two members by pulling them apart, but at the same time it will not be too cumbersome for an adult to disassemble and then assemble the two parts.

Some devices for accomplishing the above objectives are known, for example one is shown and described in Norwegian patent, NO-B-158 214, in which a bayonet-type connection is used.

The object of the present invention is to provide a pharmaceutical container and inhaler for the above purpose, which will be easy to handle for an adult but virtually impossible for a child, and that will also be sturdy and inexpensive to manufacture, such as in a plastic material.

SUMMARY OF THE INVENTION

These and other objectives are according to the invention that has a first member with one end having groove extending in a circumferential direction for connection with a second member. The second member has one end having at least one boss for engagement with the groove of the first member. The first member is provided with at least one axial notch from the groove to the end of the first member, with the groove in the vicinity of each notch being provided with at least one primary recess in the side in which the notch commences.

Normally, only one boss and one notch are provided, but improved safety can be obtained, if several bosses and notches with different pitches or evenly distributed bosses and notches are provided, so that only one of several mutual positions of the two rotatable members is the correct one for pulling the members apart.

By this design (with one boss and one notch) the two members can be easily assembled or connected by pushing them together with the boss in the notch, whereupon they are turned in relation to each other with the boss in the groove. A following attempt to disconnect or disassemble the members by pulling them apart under concurrent turning will not be successful, because the boss will be caught in the primary recess.

The invention is especially directed to an inhaler, as mentioned above. Therefore, the first member can be formed as a mouthpiece for the inhaler and the second member formed as a cap. The groove can be arranged in an outer surface of an inner sleeve on the mouthpiece and the boss on a inner surface of an outer sleeve on the cap. However, the invention could also be formed as a container only with one end of each member being closed and the other end of each member being formed for connecting the members together.

There is preferably a primary recess at either side of the notch for providing a "trap" for the boss when turning each member from either side. The "trapping" effect is enhanced in that each primary recess has a sharp side at the notch for preventing the boss from reaching the notch if a mutual pulling force is exerted on the mouthpiece and the cap. The other end of the primary recess is preferably sloping for facilitating a smooth entrance of the boss in the "trap.

Even if the boss is in the position for entering the notch from the groove, so that a pulling apart is possible, a certain resistance can be provided in that the depth of the notch is locally decreased, preferably towards its open end. This resistance can prevent a child from actually pulling the members apart.

In order to facilitate a controlled pulling apart of an adult there can be external marks on the mouthpiece and the cap for indicating when the boss is at the notch. It has been shown that such marks do not provide any guidance for a child.

It is preferred that the groove extends around the full periphery of the mouthpiece, so that the two members can be freely rotated. A secondary recess, preferably with sharp sides, can in such a case be provided substantially opposite the primary recess(es) for providing a secondary "trap" for the boss.

BRIEF DESCRIPTION OF THE DRAWINGS

The invention will be described in further detail below reference being made to the accompanying drawings, in which.

DETAILED DESCRIPTION OF INVENTION

Figure 1:
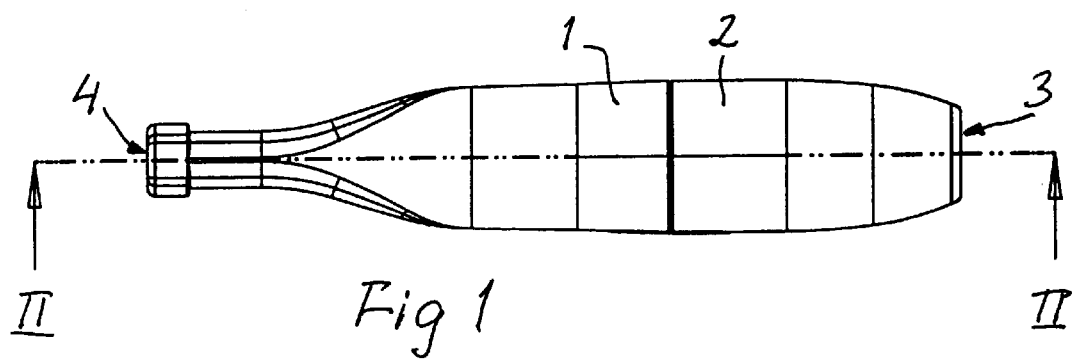
FIG. 1 is a side plan view of an inhaler embodying the invention.
Figure 6:
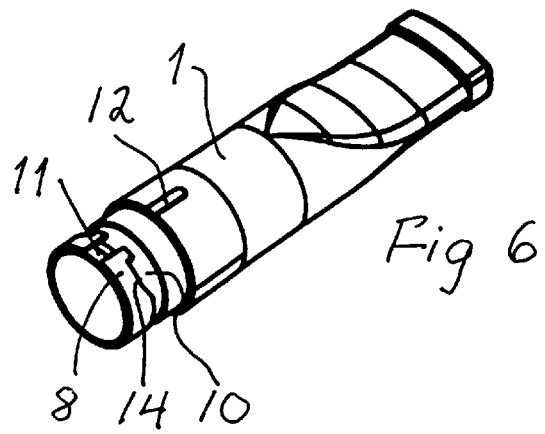
FIG. 6 is a perspective view of a mouthpiece of the inhaler according to FIG. 1.

A pharmaceutical container and inhaler device embodying the invention includes a first member, namely a mouthpiece 1, and a second member, namely a cap 2; the division line between the two members appears as a thicker line in FIG. 1. A substance to be inhaled, in the form of an ampoule (not shown) or the like, is placed in the hollow interior of the inhaler. The mouthpiece has a first flattened end 20 and a second end 22 with a circular cross-section. The cap 2 has a first end 24 for the intake of air and a second end 26 with a circular cross-section. With the exception of the flattened end 20 of the mouthpiece 1 to the left in FIG. 1, for comfortable insertion into the mouth of a user, the mouthpiece 1 and the cap 2 both have a circular cross-section, especially in the region where they are connected to each other, and they can be rotated in relation to each other.

Figure 3:
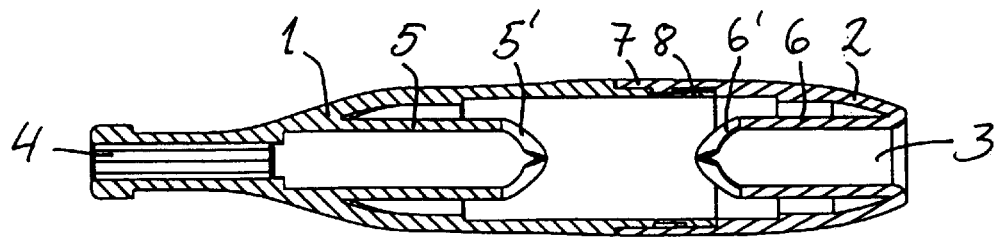
FIG. 3 is a side cross-sectional view of the inhaler of FIG. 2 along the line III—III.
Figure 2:
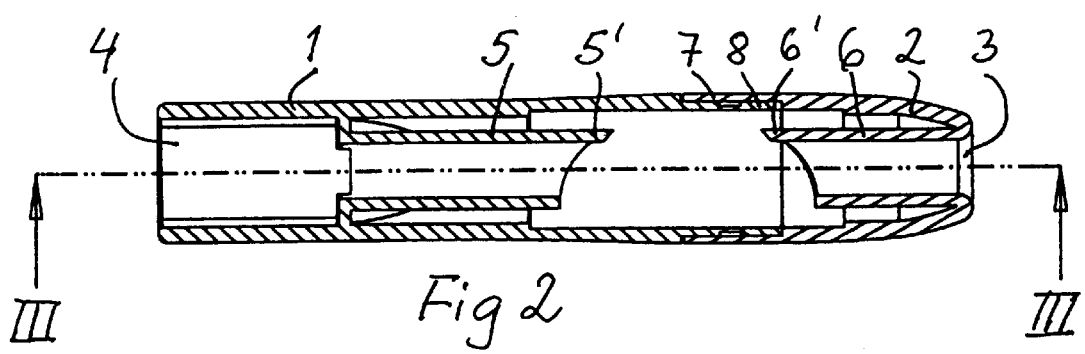
FIG. 2 is a top cross-sectional view of the inhaler of FIG. 1 along the line II—II.

The mouthpiece 1 and the cap 2 together form a tube when assembled. Accordingly, the cap 2 has a central, circular opening 3 at its first end 24 to the right in FIGS. 1–4, through which surrounding air is sucked in, whereas the mouthpiece 1 has a flattened or substantially rectangular opening 4 at its first end 20 to the left in FIGS. 1–3, through which air possibly laden with substance from the ampoule, when fitted in the inhaler, is transferred to the user's mouth.

Internally, the mouthpiece 1 and the cap 2 are provided with integral tubes 5 and 6, respectively, having sharpened ends 5' and 6', respectively, for penetrating seals at the ends of the mentioned, but not shown ampoule, when it is placed in the interior of the inhaler.

Figure 7:
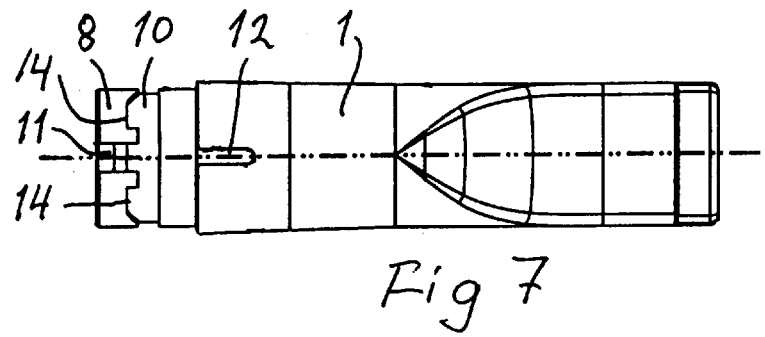
FIG. 7 is a top plan view of the mouthpiece of FIG. 6.
Figure 8:
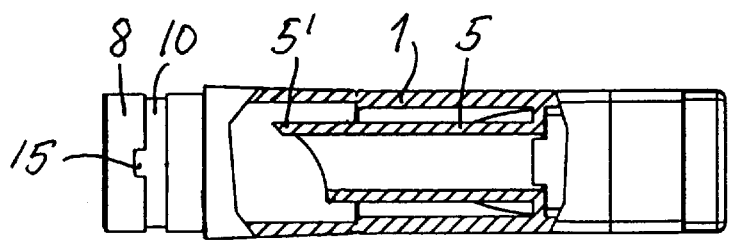
FIG. 8 is a partial cross-sectional bottom view of the mouthpiece of FIG. 6.

When assembled, the mouthpiece 1 and the cap 2 together form a generally smooth exterior surface in the region of their connection. Also their interior surface is generally smooth in the connection region. This is accomplished in that the cap 2, in its connection region at its second end 26 and to the left in FIGS. 4 and 5, has an integral outer sleeve 7 with a smaller wall thickness than the remainder of the cap 2. In the same way, the mouthpiece 1, in its connection region at its second end 22 and to the left in FIGS. 7 and 8, has an inner sleeve 8 with a smaller wall thickness than the remainder of the mouthpiece 1. The two sleeves 7 and 8 generally have the same length and fit together for forming the connection shown in FIGS. 1–3. However, the assembly and disassembly of the two members 1 and 2 can only occur in one mutual position or direction thereof for providing a child-resistance function. The invention is primarily concerned with the mechanism for obtaining this child-resistance function and is described below.

In a preferred embodiment, the mechanism for obtaining the desired connection is formed with a boss 9 in the outer sleeve 7 of the cap 2 and a circumferential groove 10 in the inner sleeve 8 of the mouthpiece 1. With the exceptions mentioned below, the width and the depth of the groove 10 is slightly larger than the axial dimension and the height, respectively, of the boss 9, so that the two members 1 and 2 can be rotated in relation to each other with the boss 9 in the groove 10. The groove 10 preferably extends a full turn around the sleeve 8, but it is also possible to have a groove that extends only a partial distance around the sleeve.

Figure 9:
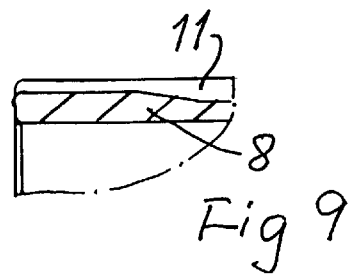
FIG. 9 is an enlarged partial cross-sectional view of a detail of the mouthpiece of FIG. 7.

There is only one exit or release from the groove 10, namely an axial notch 11 in the inner sleeve 8 of the mouthpiece 1. The width of this notch 11 exceeds the circumferential width of the boss 9. The end of the notch 11, opening into the groove 10, can have the same depth as the groove, but the notch depth can also decrease towards the end of the notch 11 or toward the second end 22 and to the left in FIG. 7. This is clearly illustrated in FIG. 9, which is an enlarged cross-sectional view through the notch 11 and shows the bottom shape of the notch. At the shallower exit or end of the notch 11 a certain resistance is provided against the movement of the boss 9 in the notch 11. In other words, a certain force is needed for pulling the mouthpiece 1 and the cap 2 apart, even if the rotational position with the boss 9 in front of the notch 11 has been found.

Assistance in positioning the boss 9 and the notch 11 is provided in that the mouthpiece 1 and the cap 2 each have an external mark 12 (FIG. 7) and 13 (FIG. 5), respectively, which are lined up in a straight line for placing the boss 9 at the notch 11. It has been shown that this indication line is not properly understood by small children.

At each side of the notch 11 there is a primary recess 14 in the forward edge (to the left in FIG. 7) of the groove 10. Each recess 14 has a second end with a sloping side facing away from the notch II and a first end with a sharp side at the notch, Thus if the mouthpiece 1 and the cap 2 when connected, are mutually rotated while also pulled apart, the boss 9 will enter the recess 14 along the sloping side but be stopped against the sharp side, so that the boss cannot find its way out through the notch 11.

Figure 4:
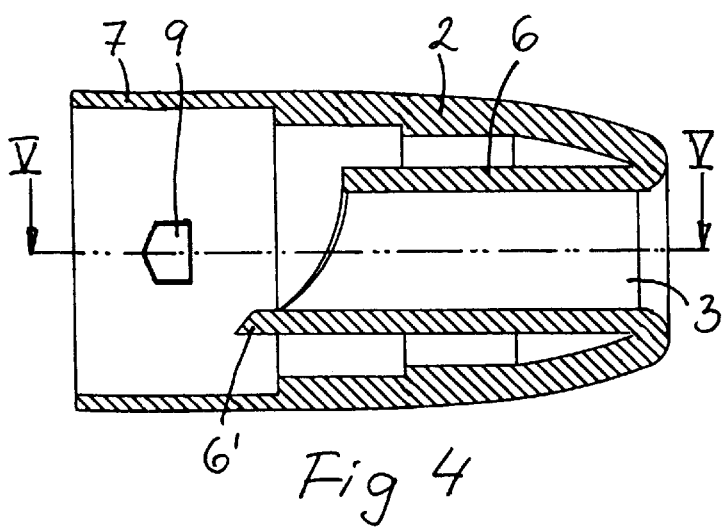
FIG. 4 is an enlarged top cross-sectional view through the cap of the inhaler of FIG. 1.
Figure 5:
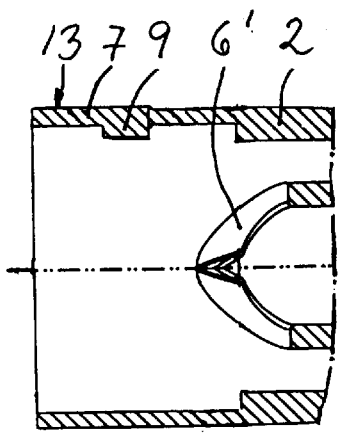
FIG. 5 is an enlarged side cross-sectional view of a portion of the cap of FIG. 4 along the line V—V.

At the side of the mouthpiece 1 generally opposite the notch 11 or toward the first end 20, the groove 10 can be provided with a secondary recess 15 providing a further locking together of the mouthpiece 1 and cap 2 if they are rotated and pulled apart in an attempt to separate the two members from each other. The side of the groove 10 opposite the notch 11 and the recesses 14 and 15 is smooth, which means that the boss 9 can slide freely against this side when the mouthpiece 1 and the cap 2 are mutually rotated but not pulled apart. As shown in FIGS. 4 and 5, the boss 9 can be generally rectangular in a top view but can have bevelled edges and a generally slightly pointed leading edge for facilitating entry into the notch 11 at assembly.

An important feature of the invention is the provision of the "trap" constituted by the primary recesses 14, and it is understood that several practical alternatives to the recesses shown and described above are possible within the scope of the claims.

The foregoing disclosure and description of the invention are illustrative and explanatory thereof, and various changes in the details of the illustrated apparatus and construction and method of operation can be made without departing from the spirit of the invention.

What is claimed is:

1. A child resistant inhaler device configured for preventing the pulling apart, without manipulation two connected, mutually rotatable members having circular cross sections in their respective areas of connection, the device comprising:

a. a first member having a first and second end, with a portion of the second end including a groove extending in a circumferential direction for connection with a second member;

b. the second member having a first and second end, with the second end including at least one boss for engagement with the groove of the first member, c. the first member having at least one substantially axial notch extending from the groove to an edge of the second end of the first member;

d. a primary recess positioned in a forward edge of the groove on each side of the axial notch and a secondary recess positioned opposite the axial notch;

e. wherein the engagement of the groove, notch and recesses allow the first and second members to be assembled and disassembled in only one mutual position in order to provide a child resistant device.

2. A device according to claim 1, wherein only one boss and one notch is provided.

3. A child resistant inhaler device configured for preventing the pulling apart, without manipulation, two connected, mutually rotatable members having circular cross sections in their respective areas of connection, the device comprising:

a. a first member formed as a mouthpiece having a first and second end, with a portion of the second end including a groove placed on an outer surface of an inner sleeve and extending in a circumferential direction for connection with a second member;

b. the second member formed as a cap having a first and second end, with the second end including at least one boss positioned on an inner surface of an outer sleeve for engagement with the groove of the first member;

c. the first member having at least one substantially axial notch extending from the groove to an edge of the second end of the first member;

d. the groove in the vicinity of each notch having at least one primary recess in a side in which the notch opens;

e. each primary recess being positioned at either side of the notch, the recess having a first end with a sharp side at the notch for preventing the boss from reaching the notch if a mutual pulling force is exerted on the mouthpiece and the cap; and d. a secondary recess positioned opposite the axial notch for providing a further locking together of the mouthpiece and the cap.

4. A device according to claim 3, wherein, a second end of each primary recess is sloping.

5. A device according to claim 3, wherein the depth of the notch is locally decreased for exerting a certain resistance on the boss.

6. A device according to any of the claims 3, 4 or 5, wherein there are external mark on the mouthpiece and the cap for indicating when the boss is positioned at the notch.

7. A device according to claim 3, wherein the boss is generally rectangular in a top view with bevelled edges and a generally slightly pointed leading edge for facilitating entrance in the notch during assembly of the mouthpiece and the cap.

* * * * *